(12) United States Patent
Michalak et al.

(10) Patent No.: US 7,842,834 B2
(45) Date of Patent: *Nov. 30, 2010

(54) PROCESS FOR THE SYNTHESIS OF SULFONYL HALIDES AND SULFONAMIDES FROM SULFONIC ACID SALTS

(75) Inventors: Ronald S. Michalak, Congers, NY (US); Jean L. Helom, Hillsdale, NJ (US); Joseph Zeldis, New City, NY (US)

(73) Assignee: Wyeth LLC, Madison, NJ (US)

( * ) Notice: Subject to any disclaimer, the term of this patent is extended or adjusted under 35 U.S.C. 154(b) by 894 days.

This patent is subject to a terminal disclaimer.

(21) Appl. No.: 11/490,389

(22) Filed: Jul. 20, 2006

(65) Prior Publication Data

US 2007/0021614 A1 Jan. 25, 2007

Related U.S. Application Data

(60) Provisional application No. 60/701,158, filed on Jul. 21, 2005.

(51) Int. Cl.
*C07C 309/24* (2006.01)
(52) U.S. Cl. .................. 562/834; 562/828
(58) Field of Classification Search ............. 562/828, 562/834
See application file for complete search history.

(56) References Cited

U.S. PATENT DOCUMENTS

| | | | |
|---|---|---|---|
| 2,199,568 A | 5/1940 | Lange et al. | |
| 2,507,408 A | 5/1950 | Jacob | |
| 2,888,486 A | 5/1959 | Gregory | |
| 4,885,027 A * | 12/1989 | Pomidor | 504/333 |
| 7,321,061 B2 * | 1/2008 | Michalak et al. | 562/828 |
| 2005/0187408 A1 | 8/2005 | Michalak et al. | |

FOREIGN PATENT DOCUMENTS

| | | |
|---|---|---|
| DE | 48 722 | 8/1889 |
| DE | 150 313 | 3/1904 |
| WO | WO03/048122 | 6/2003 |
| WO | WO 2005070904 A2 * | 8/2005 |
| WO | WO2005/082843 | 9/2005 |
| WO | WO2007/013974 | 2/2007 |

OTHER PUBLICATIONS

Abdellaoui et al., "Synthesis of the naphthalenic bioisostere of the anti-migraine drug sumatriptan," *Synthetic Communications* (1995) 25(9):1303-1311.
Abramovitch et al., "Solution and Flash Vacuum Pyrolysis of Some 2,6-Disubstituted β-Phenethylsulfonyl Azides and of β-Styrenesulfonyl Azide," *J. Org. Chem.*, 50:2066-2073 (1985).
Beilstein Registry No. 1747453, "ethanesulfonic acid methylamide, N-methyl-ethanesulfonamide," 1 page, 2008.
Beilstein Registry No. 2639938, "N-ethyl-cyclohexanesulfonamide," 1 page, 2008.
Beilstein Registry No. 2697078, "2-trifluoromethylbenzenesulfonamide," 3 pages, 2008.
Beilstein Registry No. 2702138, "4-Amino-2-trifluormethyl-benzolsulfonsaeure-(N-isopropyl-amid)," 2 pages, 2008.
Beilstein Registry No. 2703228, "4-Amino-2-trifluormethyl-benzolsulfonsaeure-(N-butyl-amid)," 2 pages, 2008.
Beilstein Registry No. 2717732, "2-Cyclohexyl-aethan-sulfonamid," 1 page, 2008.
Beilstein Registry No. 3255360, "3-phenyl-propane-1-sulfonic acid amide," 1 page, 2008.
Beilstein Registry No. 5427164, "N-methyl 2-phenylethanesulfonamide," 1 page, 2008.
Brundish et al., "Design and Synthesis of Thrombin Inhibitors: Analogues of MD-805 with Reduced Stereogenicity and Improved Potency," *J. Med. Chem.*, 42:4584-4603 (1999).
Dmowski et al., "A Site Selective Functionalisation of 1,3-Bis(trifluromethyl)benzene," *Tetrahedron*, (1998) 54:6781-92.
L. Field, "Aromatic Sulfonic Acid Anhydrides," *Journal of the American Society* (Jan. 1952) 74:394-98.
Freeman et al., "Intermediates in a peroxy acid oxidation of phenyl phenylmethanethiosulfinate[1,2]," *J Organic Chemistry* (1981) 46(20):3991-3996.
Hartman et al., "Synthesis and derivatization of novel 4-aroylthiophene-and furan-2-sulfonamides," *J Heterocyclic Chemistry* (1989) 26(6):1793-1798.
"Herstellung aromatischer Sulfonsäurechloride," *Houben-Weyl: Methoden der Organischen Chemie*, 4th Edition, George Thieme Verlag, Stuttgart, Germany, p. 563 (1955).
Huang et al., "Facile Synthesis of Sulfonyl Chlorides," *Tetrahedron Letters*, (1992) 33(19): 2657-60.
Kirk-Othmer, *Kirk-Othmer Encyclopedia of Chemical Technology*, 5th edition; www3.interscience.wiley.com/cgi-bin/mrwhome/104554789/home, 2006.
Khorana, H. G., "Carbodiimides: Part II. The Reaction of Sulphonic Acids with Carboniimides. A New Method of Preparation of Sulphonic Anhydrides," *Canadian Journal of Chemistry* (1953) 31:585-88.
Leung et al., "The difluoromethylenesulfonic acid group as a monoanionic phosphate surrogate for obtaining PTP1B inhibitors," *Bioorganic & Medicinal Chemistry* (2002) 10(7): 2309-2323.
Lichtenberger et al., "Sur les di-esters sulfoniques," *Bulletin de la Societe Chimique de France*, (1961) 363-371.
J. March, "Advanced Organic Chemistry," John Wiley & Sons, New Jersey; 4th edition (Dec. 1992); p. 499.
Nakayama et al., "Reaction of Arylmethanesulfonyl and Styrylmethanesulfonyl Chlorides with Triethylamine," *Tetrahedron Letters*, (1984) 25(40):4553-56.
Rewcastle et al., "Potential antitumor agents. 63. Structure-activity relationships for side-chain analogues of the colon 38 active agent 9-oxo-*9H*-xanthene-4-acetic acid," *J Medicinal Chemistry* (1991) 34(9):2864-2870.

(Continued)

*Primary Examiner*—Rebecca L Anderson
*Assistant Examiner*—Jason M Nolan
(74) *Attorney, Agent, or Firm*—Jennifer A. Kispert; Robert T. Ronau

(57) ABSTRACT

The present invention provides synthetic processes for the preparation of sulfonyl halides of Formula Ar—(R)$_z$—SO$_2$—X and sulfonamides of Formula Ar—(R)$_z$—SO$_2$—NR$^4$R$^5$, where the constituent variables are as defined herein, that are useful as intermediates in the preparation of pharmaceuticals.

26 Claims, No Drawings

OTHER PUBLICATIONS

*Remington's Pharmaceutical Science*, 17th edition, Easton, PA, 1985; p. 1418.

International Search Report dated Jun. 8, 2005 for International Application No. PCT/US2005/005624.

International Search Report for PCT/US2006/028182, 6 pages (Jan. 24, 2007).

Written Opinion of the International Searching Authority for PCT/US2006/028182, 8 pages (Jan. 24, 2007).

* cited by examiner

PROCESS FOR THE SYNTHESIS OF SULFONYL HALIDES AND SULFONAMIDES FROM SULFONIC ACID SALTS

This application claims benefit of priority to U.S. provisional patent application Ser. No. 60/701,158 filed on Jul. 21, 2005, which is hereby incorporated in its entirety.

FIELD OF THE INVENTION

The present invention relates to processes for the preparation of sulfonyl halides and sulfonamides useful as intermediates in the preparation of, for example, pharmaceuticals and for the preparation of sulfonamides useful as pharmaceuticals.

BACKGROUND OF THE INVENTION

Sulfonyl chlorides are widely used in the chemical industry such as for the preparation of dyes, lithographic resists, and pharmaceuticals. They can be further transformed into other functional groups such as aromatic sulfones (by Friedel-Crafts sulfonylation of aromatic substrates) or sulfonamides (by reaction with amines) (see, e.g., *Kirk-Othmer Encyclopedia of Chemical Technology*). Sulfonamides are integral functional groups of a wide variety of therapeutic small molecule drugs such as antibacterial agents, diuretics, and cPLA$_2$ inhibitors.

A typical preparation of sulfonyl chlorides involves reaction of the sodium salt of a sulfonic acid with phosphorus pentachloride, sometimes in combination with phosphorus oxychloride or thionyl chloride, frequently with heating of the reaction mixture (see, e.g., March, *Advanced Organic Chemistry*, 4$^{th}$ ed., John Wiley & Sons, 1992, p. 499). These relatively harsh reaction conditions are unsuitable for the preparation of sterically hindered sulfonyl chlorides, such as arylalkylsulfonyl chlorides and the like, which can result in low yields due to the elimination of sulfur dioxide (Nakayama et al., *Tet Lett.*, 1984, 25, 4553-4556). A milder, infrequently used method for the synthesis of sulfonyl chlorides is the reaction of tetrabutylammonium salts of sulfonic acids with triphenylphosphine/sulfuryl chloride (Widlanski et al., *Tet. Lett.*, 1992, 33, 2657-2660), a method that suffers from the disadvantage of poor atom efficiency.

Numerous sterically hindered sulfonyl halides such as (2-trifluoromethylphenyl)-methanesulfonyl chloride and other aryl- and heteroaryl-alkylsulfonyl halides are specifically useful in the preparation of cPLA$_2$ inhibitors for the treatment of asthma or arthritic and rheumatic disorders as described in, for example, WO 2003/048122. As discussed above, these intermediates can be difficult to prepare due to loss of sulfur dioxide at higher temperatures and formation of significant amounts of impurities. Thus, new and improved methods for making these compounds, and the corresponding sulfonamides, are needed. The methods provided herein help meet these and other needs.

SUMMARY OF THE INVENTION

In some embodiments, the present invention provides a synthetic process comprising reacting a compound of Formula II:

$$[Ar-(R)_z-SO_3^{-1}]_qM \qquad II$$

wherein:

Ar is C$_1$-C$_{18}$ alkyl, C$_2$-C$_{18}$ alkenyl, C$_2$-C$_{18}$ alkynyl, C$_3$-C$_{18}$ cycloalkyl, heterocycloalkyl, aryl or heteroaryl, each optionally substituted by up to five substituents independently selected from the group consisting of halogen, C$_1$-C$_6$ alkyl, C$_3$-C$_7$ cycloalkyl, heterocycloalkyl, cyano, nitro, OH, C$_1$-C$_6$ haloalkyl, C$_1$-C$_3$ perhaloalkyl, C$_1$-C$_6$ alkoxy, C$_1$-C$_6$ haloalkoxy, C-C$_3$ perhaloalkoxy, NR$^1$R$^2$, NR$^1$COR$^3$, COR$^3$, COOR$^3$, OCOR$^3$, aryloxy, heteroaryloxy, arylalkyloxy, heteroarylalkyloxy, cycloalkylalkyl, arylalkyl, heteroarylalkyl, aryl and heteroaryl;

R is C$_1$-C$_6$ alkylenyl;

each R$^1$ and R$^2$ is independently selected from the group consisting of H, C$_1$-C$_6$ alkyl and C$_3$-C$_7$ cycloalkyl;

or any R$^1$ and R$^2$ together with the N atom to which they are attached can form a 5- or 6-membered heterocycle;

each R$^3$ is independently selected from the group consisting of H, C$_1$-C$_6$ alkyl and C$_3$-C$_7$ cycloalkyl;

M is a Group I or II metal ion;

q is 1 where M is Group I metal ion;

or q is 2 where M is a Group II metal ion; and z is 0 or 1;

with a halogen substitution reagent in the presence of a catalytic amount of water and in the presence of a co-catalyst for a time and under conditions sufficient to form a compound of Formula III:

$$Ar-(R)_z-SO_2-X \qquad III$$

wherein X is halogen.

In some embodiments, the synthetic processes of the present invention further include reacting the compound of Formula III with an amine reagent, optionally in the presence of a base, for a time and under conditions sufficient to form a compound of Formula I:

$$Ar-(R)_z-SO_2-R^4R^5 \qquad I$$

wherein:

R$^4$ and R$^5$ are each, independently, H, C$_1$-C$_{18}$ alkyl, C$_2$-C$_{18}$ alkenyl, C$_2$-C$_{18}$ alkynyl, C$_3$-C$_{18}$ cycloalkyl, heterocycloalkyl, aryl or heteroaryl, each optionally substituted by up to five substituents independently selected from the group consisting of halogen, C$_1$-C$_6$ alkyl, C$_3$-C$_7$ cycloalkyl, heterocycloalkyl, cyano, nitro, OH, C$_1$-C$_6$ alkoxy, C$_1$-C$_6$ haloalkyl, C$_1$-C$_6$ haloalkoxy, aryl and heteroaryl;

or R$^4$ and R$^5$ together with the N atom to which they are attached can form a 5- or 6-membered heterocycle.

DETAILED DESCRIPTION OF EMBODIMENTS OF THE INVENTION

The present invention provides a process for the preparation of sulfonyl halides and sulfonamides, such as aryl- and heteroaryl-alkylsulfonyl halides and aryl- and heteroaryl-alkylsulfonamides, including (2-trifluoromethylphenyl)-methanesulfonyl chloride and (2-trifluoromethylphenyl)-methanesulfonamide, which are intermediates in the synthesis of certain cPLA$_2$ inhibitors. In some embodiments, the processes involve the formation of the intermediate sulfonic acid prior to conversion to the sulfonyl halide.

In some embodiments, the present invention provides a synthetic process that includes reacting a compound of Formula II:

$$[Ar-(R)_z-SO_3^{-1}]_qM \qquad II$$

wherein:

Ar is C$_1$-C$_{18}$ alkyl, C$_2$-C$_{18}$ alkenyl, C$_2$-C$_{18}$ alkynyl, C$_3$-C$_{18}$ cycloalkyl, heterocycloalkyl, aryl or heteroaryl, each optionally substituted by up to five substituents independently selected from the group consisting of halogen, C$_1$-C$_6$ alkyl, $C_3$-$C_7$ cycloalkyl, heterocycloalkyl, cyano, nitro, OH, $C_1$-$C_6$ haloalkyl, $C_1$-$C_3$ perhaloalkyl, $C_1$-$C_6$ alkoxy, $C_1$-$C_6$ haloalkoxy, $C_1$-$C_3$ perhaloalkoxy, $NR^1R^2$, $NR^1COR^3$, $COR^3$, $COOR^3$, $OCOR^3$, aryloxy, heteroaryloxy, arylalkyloxy, heteroarylalkyloxy, cycloalkylalkyl, arylalkyl, heteroarylalkyl, aryl and heteroaryl;

R is $C_1$-$C_6$ alkylenyl;

each $R^1$ and $R^2$ is independently selected from the group consisting of H, $C_1$-$C_6$ alkyl and $C_3$-$C_7$ cycloalkyl;

or any $R^1$ and $R^2$, together with the nitrogen atom to which they are attached, can form a 5- or 6-membered heterocycle;

each $R^3$ is independently selected from the group consisting of H, $C_1$-$C_6$ alkyl and $C_3$-$C_7$ cycloalkyl;

M is a Group I or II metal ion;

q is 1 where M is Group I metal ion;

or q is 2 where M is a Group II metal ion; and z is 0 or 1;

with a halogen substitution reagent in the presence of a catalytic amount of water and in the presence of a co-catalyst for a time and under conditions sufficient to form a compound of Formula III:

$$Ar—(R)_z—SO_2—X \qquad III$$

wherein X is halogen.

In some embodiments, the process of the present invention further include reacting the compound of Formula III with an amine reagent, optionally in the presence of a base, for a time and under conditions sufficient to form a compound of Formula I:

$$Ar—(R)_z—SO_2—NR^4R^5 \qquad I$$

wherein:

$R^4$ and $R^5$ are each, independently, H, $C_1$-$C_{18}$ alkyl, $C_2$-$C_{18}$ alkenyl, $C_2$-$C_{18}$ alkynyl, $C_3$-$C_{18}$ cycloalkyl, heterocyloalkyl, aryl or heteroaryl, each optionally substituted by up to five substituents independently selected from the group consisting of halogen, $C_1$-$C_6$ alkyl, $C_3$-$C_7$ cycloalkyl, heterocycloalkyl, cyano, nitro, OH, $C_1$-$C_6$ alkoxy, $C_1$-$C_6$ haloalkyl, $C_1$-$C_6$ haloalkoxy, aryl and heteroaryl;

or $R^4$ and $R^5$, together with the nitrogen atom to which they are attached, can form a 5- or 6-membered heterocycle.

In some embodiments of the processes of the present invention, the compound of Formula I is formed without isolation of the compound of Formula III.

The compound of Formula III is useful as a chemical intermediate to prepare cPLA$_2$ inhibitors, including, for example, 4-{3-[1-benzhydryl-5-chloro-2-(2-{[(3,4-dichlorobenzyl)sulfonyl]amino}ethyl)-1H-indol-3-yl]propyl}benzoic acid, 4-(3-{5-chloro-1-(diphenylmethyl)-2-[2-({[2-(trifluoromethyl)benzyl]sulfonyl}amino)ethyl]-1H-indol-3-yl}propyl)benzoic acid, 4-(3-{5-chloro-1-(diphenylmethyl)-2-[2-({[2-fluoro-6-(trifluoromethyl)benzyl]sulfonyl}amino)ethyl]-1H-indol-3-yl}propyl)benzoic acid and 4-(3-{5-chloro-1-(diphenylmethyl)-2-[2-({[2-(trifluoromethoxy)benzyl]sulfonyl}amino) ethyl]-1H-indol-3-yl}propyl)benzoic acid. Exemplary cPLA$_2$ inhibitors and methods and intermediates useful for making them are disclosed and claimed in the following applications: PCT/US2002/038311, filed Dec. 02, 2002 (published as WO 2003/048122); PCT/US2004/023247, filed Jul. 19, 2004 (published as WO 2005/012238); PCT/US2004/038335, filed Nov. 16, 2004 (published as WO 2005/049566); PCT/US2005/005624, filed Feb. 23, 2005 (published as WO 2005/082843); PCT/US2005/009746, filed Mar. 14, 2005 (published as WO 2005/097727); PCT/US2005/029338, filed Aug. 18, 2005 (published as WO 2006/023611); U.S. patent application Ser. No. 10/930,534 (filed Aug. 31, 2004); U.S. patent application Ser. No. 10/948,004 (filed Sep. 23, 2004); and U.S. patent application Ser. No. 11/442,199 (filed May 26, 2006), each of which is incorporated herein by reference in its entirety. In some embodiments, the present invention provides processes for preparing such cPLA$_2$ inhibitors which comprise preparing a compound of Formula III in accordance with a process of the invention and converting the compound of Formula III into the cPLA$_2$ inhibitor. In some embodiments, the cPLA$_2$ inhibitors include 4-{3-[1-benzhydryl-5-chloro-2-(2-{[(3,4-dichlorobenzyl)sulfonyl]amino}ethyl)-1H-indol-3-yl]propyl}benzoic acid, 4-(3-{5-chloro-1-(diphenylmethyl)-2-[2-({[2-(trifluoromethyl)benzyl]sulfonyl}amino)ethyl]-1H-indol-3-yl}propyl) benzoic acid, 4-(3-{5-chloro-1-(diphenylmethyl)-2-[2-({[2-fluoro-6-(trifluoromethyl)benzyl]sulfonyl}amino)ethyl]-1H-indol-3-yl}propyl)benzoic acid and 4-(3-{5-chloro-1-(diphenylmethyl)-2-[2-({[2-(trifluoromethoxy)benzyl]sulfonyl}amino) ethyl]-1H-indol-3-yl}propyl)benzoic acid.

In some embodiments, the present invention provides processes for the preparation of cPLA$_2$ inhibitors having Formula (A1):

(A1)

wherein:

Ar, R and z are as defined in claim 1;

$R^{10}$ is selected from the formulae —$(CH_2)_n$-A, —$(CH_2)_n$—S-A, or —$(CH_2)_n$—O-A, wherein A is selected from the moieties:

wherein:

D is $C_1$-$C_6$ alkyl, $C_1$-$C_6$ alkoxy, $C_3$-$C_6$ cycloalkyl, —$CF_3$ or —$(CH_2)_{1-3}$—$CF_3$;

B and C are independently selected from phenyl, pyridinyl, pyrimidinyl, furyl, thienyl and pyrrolyl groups, each optionally substituted by from 1 to 3, preferably 1 to 2, substituents selected independently from H, halogen, —CN, —CHO, —$CF_3$, —$OCF_3$, —OH, —$C_1$-$C_6$ alkyl, $C_1$-$C_6$ alkoxy, —$NH_2$, —$N(C_1$-$C_6$ alkyl)$_2$, —$NH(C_1$-$C_6$ alkyl), —N—C(O)—($C_1$-$C_6$ alkyl), —$NO_2$, or by a 5- or 6-membered heterocyclic or heteroaromatic ring containing 1 or 2 heteroatoms selected from O, N or S;

n is an integer from 0 to 3;

$n_1$ is an integer from 1 to 3;

$n_3$ is an integer from 0 to 3;

$n_4$ is an integer from 0 to 2

$X^2$ is selected from —O—, —CH$_2$—, —S—, —SO—, —SO$_2$—, —NH—, —C(O)—,

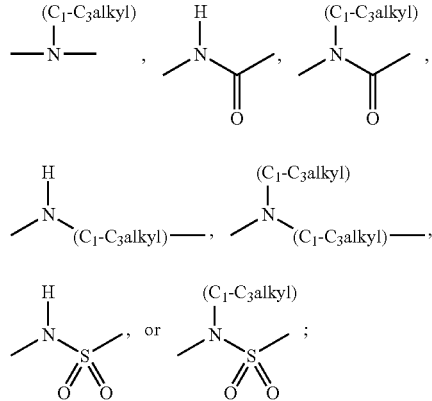

$R^{12}$ is a ring moiety selected from phenyl, pyridinyl, pyrimidinyl, furyl, thienyl or pyrrolyl groups, the ring moiety being substituted by a group of the formula —(CH$_2$)$_{n4}$—CO$_2$H or a pharmaceutically acceptable acid mimic or mimetic; and also optionally substituted by 1 or 2 additional substituents independently selected from H, halogen, —CN, —CHO, —CF$_3$, —OCF$_3$, —OH, —C$_1$-C$_6$ alkyl, C$_1$-C$_6$ alkoxy, C$_1$-C$_6$ thioalkyl, —NH$_2$, —N(C$_1$-C$_6$ alkyl)$_2$, —NH(C$_1$-C$_6$ alkyl), —N—C(O)—(C$_1$-C$_6$ alkyl), or —NO$_2$;

$R^{13}$ is selected from H, halogen, —CN, —CHO, —CF$_3$, —OCF$_3$, —OH, —C$_1$-C$_6$ alkyl, C$_1$-C$_6$ alkoxy, C$_1$-C$_6$ thioalkyl, —NH$_2$, —N(C$_1$-C$_6$ alkyl)$_2$, —NH(C$_1$-C$_6$ alkyl), —N—C(O)—(C$_1$-C$_6$ alkyl), or —NO$_2$;

$R^{14}$ is selected from H, halogen, —CN, —CHO, —CF$_3$, —OCF$_3$, —OH, —C$_1$-C$_6$ alkyl, C$_1$-C$_6$ alkoxy, C$_1$-C$_6$ thioalkyl, —NH$_2$, —N(C$_1$-C$_6$ alkyl)$_2$, —NH(C$_1$-C$_6$ alkyl), —N—C(O)—(C$_1$-C$_6$ alkyl), —NO$_2$, —N—C(O)—N(C$_1$-C$_3$ alkyl)$_2$, —N—C(O)—NH(C$_1$-C$_3$ alkyl), —N—C(O)—O—(C$_1$-C$_3$ alkyl), —SO$_2$—C$_1$-C$_6$ alkyl, —S—C$_3$-C$_6$ cycloalkyl, —S—CH$_2$—C$_3$-C$_6$ cycloalkyl, —SO$_2$—C$_3$-C$_6$ cycloalkyl, —SO$_2$—CH$_2$—C$_3$-C$_6$ cycloalkyl, C$_3$-C$_6$ cycloalkyl, —CH$_2$—C$_3$-C$_6$ cycloalkyl, —O—C$_3$-C$_6$ cycloalkyl, —O—CH$_2$—C$_3$-C$_6$ cycloalkyl, phenyl, benzyl, benzyloxy, morpholino or other heterocycles such as pyrrolidino, piperidine, piperizine furan, thiophene, imidazole, tetrazole, pyrazine, pyrazolone, pyrazole, imidazole, oxazole or isoxazole, the rings of each of these $R^{14}$ groups each being optionally substituted by from 1 to 3 substituents selected from the group of H, halogen, —CN, —CHO, —CF$_3$, —OH, —C$_1$-C$_6$ alkyl, C$_1$-C$_6$ alkoxy, —NH$_2$, —N(C$_1$-C$_6$ alkyl)$_2$, —NH(C$_1$-C$_6$ alkyl), —N—C(O)—(C$_1$-C$_6$ alkyl), —NO$_2$, —SO$_2$(C$_1$-C$_3$ alkyl), —SO$_2$NH(C$_1$-C$_3$ alkyl), —SO$_2$N(C$_1$-C$_3$ alkyl)$_2$, or OCF$_3$; or a pharmaceutically acceptable salt form thereof. In some embodiments, $R^{10}$ is diphenylmethyl.

In some embodiments, the compound having Formula (A1) or a pharmaceutically acceptable salt thereof is prepared by the compound having formula III is reacted with a compound having Formula (B1):

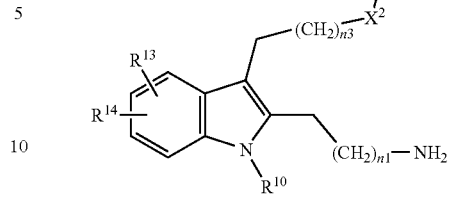

wherein $R^{12}$ is a ring moiety selected from phenyl, pyridinyl, pyrimidinyl, furyl, thienyl or pyrrolyl groups, the ring moiety being substituted by a group of the formula —(CH$_2$)$_{n4}$—CO$_2$H wherein the carboxy group is optionally protected by a protecting group and the ring moiety being also optionally substituted by 1 or 2 additional substituents independently selected from H, halogen, —CN, —CHO, —CF$_3$, —OCF$_3$, —OH, —C$_1$-C$_6$ alkyl, C$_1$-C$_6$ alkoxy, C$_1$-C$_6$ thioalkyl, —NH$_2$, —N(C$_1$-C$_6$ alkyl)$_2$, —NH(C$_1$-C$_6$ alkyl), —N—C(O)—(C$_1$-C$_6$ alkyl), or —NO$_2$; and $R^{10}$, $R^{13}$, $R^{14}$, $X^2$, $n_1$, $n_3$ and $n_4$ are as defined above to give a sulfonamide and, if the carboxy group is protected by a protecting group, the protecting group is removed from the resultant sulfonamide.

The compounds having the formula II: [Ar—(R)$_z$—SO$_3^{-1}$]$_q$M where Ar, R, and q are as defined above and z is 1 may be prepared as described in WO 2005/082843, which is incorporated herein by reference in its entirety.

A general outline of some embodiments of the processes of the present invention is provided in Scheme I, where constituent members of the depicted compounds of Formulas I, II and III are defined hereinabove.

Scheme I

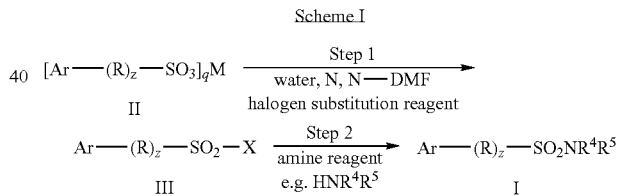

As shown in Step 1 of Scheme I, sulfonic acid salts of Formula II can be converted to sulfonyl halides of Formula III by reaction with a halogen substitution reagent in the presence of a catalytic amount of water and in the presence of a co-catalyst such as N,N-dimethylformamide.

Halogen substitution reagents, as used herein, are reagents that can convert a non-halogen substituent of the compound of Formula II (such as, for example, H, OH or OM) to a halogen substituent. Halogen substitution reagents of the present invention can, for example, convert a sulfonic acid salt moiety or sulfonic acid moiety to a sulfonyl halide moiety. Numerous reagents capable of carrying out the conversion of sulfonyl acid to sulfonyl halide are known in the art. Some preferred halogen substitution reagents include SOCl$_2$, POCl$_3$, CCl$_4$/triphenylphosphine, oxalyl chloride and oxalyl bromide. In some more preferred embodiments, the halogen substitution reagent is oxalyl chloride. Generally, the halogen substitution reagent is used in a molar excess, relative to the compound of Formula II. Preferably, the halogen substitution reagent is employed in an amount of about 1.2 equivalents or greater, relative to the amount of compound of Formula II. For example, oxalyl chloride can be used as the halogen substitution reagent in molar excess, for example from about 1.2 to about 4 equivalents; about 2 to about 3 equivalents or about 2.1 to about 2.6 equivalents with respect to the amount of sulfonic acid salt reagent (compound of Formula II). One skilled in the art will recognize that the amount of halogen substitution reagent used will depend, inter alia, on the amount of solvent and the nature and reactivity of the starting materials and solvents.

As shown in step 1 of Scheme 1, the reaction of the compound of Formula II and the halogen substitution reagent is carried out in the presence of a catalytic amount of water. While not wishing to be bound by any particular theory, it is believed that the catalytic amount of water facilitates the formation of the sulfonyl chloride from the sodium salt by first forming the corresponding protonated sulfonic acid, which is easier to convert to the sulfonyl chloride and can be done under milder conditions, such as by using oxalyl chloride at room temperature or below. The molar ratio of the catalytic amount of water to the compound of Formula II is generally less than about 0.5:1, or from about 0.2:1 to about 0.4:1, or about 0.3:1.

Generally, the reaction of the compound of Formula II with the halogen substitution reagent is carried out in the presence of a co-catalyst. While not wishing to be bound by any particular theory, it is believed that the co-catalyst facilitates the formation of the sulfonyl chloride. Suitable co-catalysts include N, N-dialkylformamides, for example N,N-dimethylformamide, as well as other reagents useful as co-catalysts for sulfonic acid halogenation reactions, for example triphenylphosphine oxide. The co-catalyst is generally provided in an amount sufficient to accelerate the reaction rate. In some embodiments, the co-catalyst is present in less than about one equivalent relative to the amount of sulfonic acid salt reagent. In some preferred embodiments, the co-catalyst is present in an amount of about 0.01 to about 0.5 equivalents, or about 0.1 to about 0.2 equivalents, relative to the amount of sulfonic acid salt reagent. One skilled in the art will recognize that the amount of the co-catalyst used will depend, inter alia, on the amount of solvent and the nature and reactivity of the starting materials and solvents.

In some embodiments, the reacting of the compound of Formula II with the halogen substitution reagent is carried out in a solvent system that includes at least one organic solvent. In some embodiments, the solvent system can include two or more solvents. Solvents suitable for inclusion in the solvent system include aprotic organic solvents, polar aprotic organic solvents, nonpolar aprotic organic solvents, water-miscible aprotic organic solvents, and water-immiscible aprotic organic solvents. In some embodiments, the solvent system includes one or more of tetrahydrofuran, acetonitrile, N,N-dimethylformamide, dioxane, acetone, toluene, methylene chloride, 1,2-di-chloroethane, methyl t-butyl ether and ethyl ether. In some preferred embodiments, the solvent system includes or consists of tetrahydrofuran.

The halogen substitution reaction can be carried out at any suitable temperature. Generally, the reaction is performed at a temperature below room temperature. For example, in some embodiments, the reaction can be carried out at or below about 5° C., for example at a temperature of from about 0° C. to about 5° C.

In accordance with some embodiments of the invention, and as shown in Step 2 of Scheme I, the sulfonyl halides of Formula III can react with an amine reagent, optionally in the presence of a base, for a time and under conditions sufficient to form a compound of Formula I:

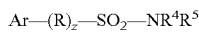

$$Ar-(R)_z-SO_2-NR^4R^5$$

where the constituent variables are as defined herein.

Advantageously, in accordance with some embodiments of the invention, the sulfonyl halide of Formula III need not be isolated prior to reaction with the amine reagent.

Generally, where excess halogen substitution reagent is employed for the reaction with the compound of Formula II, it is advantageous that the excess halogen substitution reagent remaining after the reaction be either removed or destroyed, prior to reaction of the sulfonyl halide with the amine reagent, to prevent the formation of impurities. In some embodiments, the excess halogen substitution reagent can be destroyed by adding a chemical reagent, for example a small amount of water. Preferably, a minimum amount of water should be used to destroy the excess halogen substitution reagent, such as oxalyl chloride, when the sulfonyl halides of Formula III, such as (2-trifluoromethyl-phenyl)-methanesulfonyl chloride, are sensitive to hydrolysis. Alternatively, the excess halogen substitution reagent can be removed, for example by one or more of distillation; distillation under reduced pressure; distillation further facilitated by adding a co-solvent; or distillation under reduced pressure further facilitated by adding a co-solvent. When the excess halogen substitution reagent is removed by distillation, it is not necessary that the distillation be continued to dryness.

As used herein, the term "amine reagent" is intended to mean a reagent that either is an amine capable of participating in the reaction with the compound of Formula III to produce a sulfonamide of Formula I, or a reagent that provides such an amine. In some embodiments, the amine reagent has the Formula $HNR^4R^5$, where $R^4$ and $R^5$ are as defined supra. Thus, amine reagents include ammonia, primary and secondary amines, as well as reagents that are capable of liberating or producing an amine of the Formula $HNR^4R^5$, such as $NH_4OH$. In some embodiments, the amine reagent can be in a pure form such as gaseous ammonia or dimethylamine. In some preferred embodiments, the amine reagent is gaseous ammonia, or $NH_4OH$.

In the amination step of Scheme 1, when excess amount of the amine reagent is used, an ammonium halide inorganic salt can be formed. Such ammonium halide inorganic salts can be conveniently removed from the reaction solution by standard techniques, for example by filtration.

The amination of the compound of Formula III (as shown in Step 2 of Scheme 1) can be carried out in a solvent system that can include one or more organic solvents; for example a single organic solvent, or a mixture of two or more organic solvents. Suitable solvents for inclusion in the solvent system include one or more of tetrahydrofuran, acetonitrile, N,N-dimethylformamide, dioxane, acetone, toluene, methylene chloride, 1,2-di-chloroethane, methyl t-butyl ether and ethyl ether.

In some embodiments, the solvent system for the amination includes, in addition to any organic solvents, a small amount of water. It is believed that the presence of a small amount of water in the solvent system facilitates the dissolving the amine reagent. It is advantageous to keep the amount of water in the solvent system at a minimum if the sulfonyl halides of Formula III, such as (2-trifluoromethyl-phenyl)-methanesulfonyl chloride, are sensitive to hydrolysis. For example, in some embodiments, the amount of water is present in less than about one equivalent relative to the amount of sulfonyl halide reagent. One preferred solvent system includes a small amount of water and tetrahydrofuran.

In some embodiments, the reaction of the compound of Formula III and the amine reagent is performed in the presence of a base. Suitable bases include ammonia, lower (i.e., $C_{1-6}$) trialkyl amines, pyridine, or an inorganic base such as metallic carbonates or bicarbonates. In many instances, it is preferred that the amine reagent also function as the base, particularly where the amine reagent is ammonia, or relatively small in size, for example a lower (i.e., $C_{1-6}$) mono- or di-alkyl amine.

The reaction of the compound of Formula III with the amine reagent can be carried out at any suitable temperature. Generally, the reaction is performed at a temperature below room temperature. For example, in some embodiments, the reaction can be carried out at a temperature of less than about $-10°$ C. In some preferred embodiments, the reaction can be carried out at a temperature of from about $-20°$ C. to about $-10°$ C.

The sulfonic acid salts of Formula II can be any of a variety of organic sulfonic acid salts. In some embodiments, Ar in the compound of Formula III is phenyl optionally substituted by up to five substituents independently selected from the group consisting of halogen, $C_1$-$C_6$ alkyl, $C_3$-$C_7$ cycloalkyl, heterocycloalkyl, cyano, nitro, OH, $C_1$-$C_6$ haloalkyl, $C_1$-$C_3$ perhaloalkyl, $C_1$-$C_6$ alkoxy, $C_1$-$C_6$ haloalkoxy, $C_1$-$C_3$ perhaloalkoxy, $NR^1R^2$, $NR^1COR^3$, $COR^3$, $COOR^3$, $OCOR^3$, aryloxy, heteroaryloxy, arylalkyloxy, heteroalkyloxy, cycloalkylalkyl, arylalkyl, heteroarylalkyl, cycloalkylalkyl, arylalkyl, heteroarylalkyl, aryl and heteroaryl.

In some embodiments, Ar in the compound of Formula III is phenyl substituted by up to five substituents independently selected from the group consisting of $C_1$-$C_6$ alkyl, $C_1$-$C_6$ haloalkyl, $C_1$-$C_3$ perhaloalkyl, $C_1$-$C_6$ alkoxy, $C_1$-$C_6$ haloalkoxy, $C_1$-$C_3$ perhaloalkoxy, halogen, CN, $NO_2$, $NR^1R^2$ and $NR^1COR^3$.

In some embodiments, Ar in the compound of Formula III is a disubstituted phenyl group bearing substituents in the 2- and 6-positions; or a disubstituted phenyl group bearing substituents in the 3- and 4-positions; or a monosubstituted phenyl group bearing a substituent in the 2-position. In some embodiments, the substituents are independently selected from halogen, for example chlorine, $C_{1-6}$ alkyl, for example methyl, $C_{1-6}$ alkoxy, for example methoxy, $C_{1-3}$ perhaloalkyl, for example trifluoromethyl and $C_{1-3}$ perhaloalkoxy, for example trifluoromethoxy.

In some embodiments, Ar in the compound of Formula III is phenyl substituted by up to three groups independently selected from $C_1$-$C_6$ haloalkyl, $C_1$-$C_3$ perhaloalkyl and $C_{1-3}$ perhaloalkoxy. In some embodiments, Ar in the compound of Formula III is phenyl substituted with one perhaloalkyl group at the 2 position thereof. In some embodiments, Ar in the compound of Formula III is 2-trifluoromethylphenyl. In other embodiments, Ar in the compound of Formula III is phenyl substituted with one perhaloalkoxy group at the 2 position thereof, for example, 2-trifluoromethoxyphenyl. In still other embodiments, Ar in the compound of Formula III is phenyl substituted with two halogens at the 3 and 4 positions thereof, for example, 3,4-dichlorophenyl. In further embodiments, Ar in the compound of Formula III is phenyl substituted with groups in the 2 and 6 positions thereof, for example, 2-fluoro-6-(trifluoromethyl)phenyl.

In some embodiments, z is 1. In some further embodiments, z is 1, and R is $C_1$-$C_4$ alkylene, for example methylene.

In some embodiments, X is Cl. In some embodiments, M is $Na^+$ ion or $K^+$ ion, preferably $Na^+$ ion.

In some embodiments, Ar is phenyl substituted with one perhaloalkyl group at the 2 position thereof; R is methylene or ethylene; M is $Na^+$ ion or $K^+$ ion; X is Cl; q is 1; and z is 1.

In some embodiments of the synthetic process of the present invention, the co-catalyst is N,N-dimethylformamide; the halogen substitution reagent is oxalyl chloride; and the molar ratio of the catalytic amount of water to the compound of Formula II is of a value of between about 0.2 to about 0.4.

In some embodiments of the synthetic process of the present invention, Ar is phenyl substituted with one perhaloalkyl group at the 2 position thereof; R is methylene or ethylene; M is $Na^+$ ion or $K^+$ ion; X is Cl; q is 1; z is 1; the co-catalyst is N,N-dimethylformamide; the halogen substitution reagent is oxalyl chloride; the molar ratio of the halogen substitution reagent to the compound of Formula II is at a value of about 2 to about 3; and the molar ratio of the catalytic amount of water to the compound of Formula II is of a value of between about 0.2 to about 0.4.

In some embodiments of the process of forming the compound of Formula I, the amine reagent is gaseous ammonia, and the reacting of the compound of Formula III with the amine reagent is carried out in a solvent system comprising an organic solvent and a small amount of water.

In some embodiments of the process of forming the compound of Formula I, the process of the present invention further comprises isolating the compound of Formula I.

In some embodiments of the processes of the invention, Ar is phenyl substituted with one perhaloalkyl group at the 2 position thereof; R is methylene or ethylene; M is $Na^+$ ion or $K^+$ ion; X is Cl; q is 1; z is 1; the co-catalyst is N,N-dimethylformamide; the halogen substitution reagent is oxalyl chloride; the molar ratio of the halogen substitution reagent to the compound of Formula II is at a value of about 2 to about 3; the molar ratio of the catalytic amount of water to the compound of Formula II is of a value of between about 0.2 to about 0.4; and the compound of Formula I is formed without isolation of said compound of Formula III. In some further embodiments, Ar is 2-trifluoromethylphenyl.

In some embodiments, the processes of the present invention further include a) removing excess the halogen substitution reagent; and c) isolating the compound of Formula I.

In some embodiments, of each of the processes of the invention, the compound of Formula I is formed without isolation of the compound of Formula III.

The compounds of Formula I can be isolated from the reaction mixture by any routine method such as precipitation and filtration. Any of numerous well known methods for inducing precipitation can be used. In some embodiments, the reaction mixture can be cooled (e.g., less than about $10°$ C.) to help induce precipitation. In some embodiments, an anti-solvent such as water or a solvent containing water can be added to the reaction mixture to induce precipitation. In some embodiments, precipitation can be facilitated by lowering the temperature of the reaction mixture to, for example, below about $5°$ C.

Numerous advantages of the present invention are apparent to the art-skilled. For example, preparation of sulfonyl halide at a moderate temperautre allows for improved yields by avoiding the hydrolysis of sulfonyl halides in the presence of water. Additionally, the preparation and isolation methods described herein help maximize yields.

In some embodiments of the invention, multi-step processes are carried out stepwise and each intermediate is isolated before proceeding to the next step. In other embodiments of the invention, some of the intermediates are isolated and others are not. In yet other embodiments, none of the intermediates are completely isolated and all of the reactions take place in a single reactor vessel.

It is understood in the generic description above and for other groups described herein that, in each instance any variable group may be independently substituted by their allowed groups. Thus, for example, where a structure is described wherein two substituents selected from a same group are simultaneously present on the same compound, the two substituents can be different members of the same group.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "alkyl", employed alone, is defined herein as, unless otherwise stated, either a straight-chain or branched saturated hydrocarbon moiety. In some embodiments, the alkyl moiety contains 1 to 18, 1 to 12, 1 to 10, 1 to 8, 1 to 6, or 1 to 4 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like.

The term "alkylenyl" refers to a bivalent straight-chained or branched alkyl group.

As used herein, "alkenyl" refers to an alkyl group having one or more carbon-carbon double bonds. Nonlimiting examples of alkenyl groups include ethenyl, propenyl, and the like.

As used herein, "alkynyl" refers to an alkyl group having one or more carbon-carbon triple bonds. Nonlimiting examples of alkynyl groups include ethynyl, propynyl, and the like.

As used herein, "haloalkyl" refers to an alkyl group having one or more halogen substituents, up to and including perhalogenated species. Thus, examples of haloalkyl groups include perhaloalkyl groups such as $CF_3$, $C_2F_5$, $CCl_3$, $C_2Cl_5$, and the like, as well as groups having less than perhalo substitution, such as $CHF_2$, $CHCl_2$ and the like. The term "perhaloalkyl" is intended to denote an alkyl group in which all of the hydrogen atoms are replaced with halogen atoms.

The term "alkoxy", employed alone or in combination with other terms, is defined herein as, unless otherwise stated, —O-alkyl. Examples of alkoxy moieties include, but are not limited to, chemical groups such as methoxy, ethoxy, isopropoxy, sec-butoxy, tert-butoxy, and the like.

The term "haloalkoxy", employed alone or in combination with other terms, is defined herein as, unless otherwise stated, —O-haloalkyl. Examples of haloalkoxy moieties include, but are not limited to, chemical groups such —$OCF_3$, and the like.

The term "cycloalkyl", employed alone or in combination with other terms, is defined herein as, unless otherwise stated, a monocyclic, bicyclic, tricyclic, fused, bridged, or spiro monovalent non-aromatic hydrocarbon moiety of 3-18 or 3-7 carbon atoms. Also included in the definition of cycloalkyl are moieties that have one or more aromatic rings fused (i.e., having a bond in common with) to the nonaromatic ring. Any suitable ring position of the cycloalkyl moiety can be covalently linked to the defined chemical structure. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, and the like.

As used herein, "heterocycloalkyl" refers to a cycloalkyl group (e.g. of 3-12 atoms) wherein one or more (e.g., up to 4 atoms) are replaced by a heteroatom such as an O, S, N or P atom. Also included in the definition of heterocycloalkyl are moieties that have one or more (e.g., two) aromatic rings fused (i.e., having a bond in common with) to the nonaromatic heterocyclic ring, for example phthalimidyl, naphthalimidyl pyromellitic diimidyl, phthalanyl, and benzo derivatives of saturated heterocycles such as indolene and isoindolene groups. In some embodiments, heterocycloalkyl groups are 3-12 membered groups having 1-4 heteroatoms independently selected from oxygen, nitrogen and sulfur, and optionally having one or two benzene rings fused thereto, where the group is bonded via a ring carbon or a nitrogen atom.

The terms "halo" or "halogen", employed alone or in combination with other terms, is defined herein as, unless otherwise stated, fluoro, chloro, bromo, or iodo.

The term "aryl", employed alone or in combination with other terms, is defined herein as, unless otherwise stated, an aromatic hydrocarbon of up to 14 carbon atoms, which can be a single ring (monocyclic) or multiple rings (bicyclic, up to three rings) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like.

The term "aryloxy" as used herein means a group of formula —O-aryl, where the term "aryl" has the definition as previously described herein.

The term "arylalkyl" or "aralkyl," employed alone or in combination with other terms, is defined herein as, unless otherwise stated, an alkyl group as herein before defined, that is substituted with an aryl moiety as defined herein. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and the like.

The term "arylalkyloxy" as used herein means a group of formula —O-arylalkyl, where the term "arylalkyl" has the definition as previously described herein.

As used herein, "heteroaryl" groups are monocyclic and polycyclic (e.g., two or three rings) aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms. In some embodiments, heteroaryl is an aromatic 5-24 membered mono- or poly- (e.g., di- or tri-)cyclic group having 1-4 heteroatoms the same or different selected from oxygen, nitrogen and sulfur.

The term "heteroarylalkyl," employed alone or in combination with other terms, is defined herein as, unless otherwise stated, an alkyl group as herein before defined, substituted with a heteroaryl moiety as defined herein. Examples of heteroarylalkyl moieties include, but are not limited to, chemical groups such as pyridylmethyl.

The term "heteroarylalkyloxy" as used herein means a group of formula —O-heteroarylalkyl, where the term "heteroarylalkyl" has the definition as previously described herein.

As used herein, "heterocycle" refers to a heteroaryl or heterocycloalkyl group.

The term "heteroaryloxy" as used herein means a group of formula —O-heteroaryl, where the term "heteroaryl" has the definition as previously described herein.

As used herein, the term "reacting" refers to the bringing together of designated chemical reactants such that a chemical transformation takes place generating a compound different from any initially introduced into the system. Reacting can take place in the presence or absence of solvent.

As used herein, the term "precipitating" is used as known in the art and generally refers to the formation of solid (e.g., precipitate) from a solution in which the solid is dissolved. The solid can be amorphous or crystalline. Methods of precipitation are well known in the art and include, for example, increasing the proportion of solvent in which a solute is insoluble, decreasing temperature, chemically transforming the solute such that it becomes no longer soluble in its solvent, and the like.

The compounds of the present invention can contain an asymmetric atom, and some of the compounds can contain one or more asymmetric atoms or centers, which can thus give rise to optical isomers (enantiomers) and diastereomers. The present invention includes such optical isomers (enantiomers) and diastereomers (geometric isomers), as well as, the racemic and resolved, enantiomerically pure R and S stereoisomers, as well as, other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The reactions of the processes described herein can be carried out in air or under an inert atmosphere. Typically, reactions containing reagents or products that are substantially reactive with air can be carried out using air-sensitive synthetic techniques that are well known to the skilled artisan.

Upon carrying out preparation of compounds according to the processes described herein, the usual isolation and purification operations such as concentration, filtration, extraction, solid-phase extraction, recrystallization, chromatography, and the like may be used to isolate the desired products.

The invention will be described in greater detail by way of specific examples. The following example is offered for illustrative purposes, and are not intended to limit the invention in any manner. Those of skill in the art will readily recognize a variety of noncritical parameters which can be changed or modified to yield essentially the same results.

EXAMPLE 1

Synthesis of (2-Trifluoromethyl-phenyl)-methanesulfonamide

A vessel of suitable size was charged with tetrahydrofuran (THF, 250 mL), water (1 mL), DMF (2 mL), and (2-trifluoromethyl-phenyl)-methanesulfonic acid, sodium salt (50 g, 0.190 mol). The mixture was stirred under a nitrogen blanket and cooled to 0-5° C. Oxalyl chloride (63 g, 0.496 mol) was added dropwise to the reaction mixture. The mixture was stirred at 0-5° C. for 16 hours. In-process analysis (HPLC) showed a 99% conversion to (2-(trifluoromethyl)phenyl) methanesulfonyl chloride.

The reaction mixture was concentrated to 107 g, then diluted with THF (200 mL). The mixture was stirred and cooled to −10 to −20° C. Water (3.0 mL) was added dropwise. Ammonia (gas, 13 g, 0.765 mol) was added via subsurface tubing to the reaction mixture. The reaction mixture was basic to pH paper. In-process testing (HPLC) showed complete conversion of the sulfonyl chloride to the sulfonamide with ~5% of the sulfonic acid. The mixture was filtered to remove inorganic salts. Water (135 mL) was added to the filtrate. The filtrate was concentrated to 190 g. The mixture was stirred at 0-5° C. for 30 min. The solid product was collected by filtration and dried to constant weight to give 33.2 g (73%) of the title compound. $^1$HNMR (300 MHz, CDCl$_3$): δ 7.81-7.52 (m, 4H, ArH), 4.60 (s, 2H, CH$_2$), and 4.52 (br s, 2H, NH$_2$).

EXAMPLE 2

Synthesis of 4-(3-{5-chloro-1-(diphenylmethyl)-2-[2-({[2(trifluoromethyl)benzyl]sulfonyl}amino) ethyl]-1H-indol-3-yl}propyl)benzoic acid Step 1: To a suspension of 4-{3-[2-(2-aminoethyl)-1-benzhydryl-5-chloro-1H-indol-3-yl]propyl}benzoic acid (prepared as described in U.S. Pat. No. 6,797,708, incorporated herein by reference in its entirety) (10.0 g, 19 mmol) in CH$_3$CN (100 mL) and MeOH (25 mL) was added (trimethylsilyl)diazomethane (2.0 M soln. in hexanes, 9.6 mL, 19 mmol). After 16 h the mixture was filtered and concentrated to afford the methyl 4-{3-[2-(2-aminoethyl)-1-benzhydryl-5-chloro-1H-indol-3-yl]propyl}benzoate (8.8 g, ca. 86%), an orange foam, which was used without purification.

Step 2: Methyl 4-{3-[2-(2-aminoethyl)-1-benzhydryl-5-chloro-1H-indol-3-yl]propyl}benzoate (Example 2, Step 1, 9.1 g, 17 mmol) was treated with (2-(trifluoromethyl) phenyl)methanesulfonyl chloride (4.8 g, 17 mmol, obtainable according to example 1 above) and sat. NaHCO$_3$ in CH$_2$Cl$_2$. The mixture was poured into saturated sodium bicarbonate and extracted with CH$_2$Cl$_2$. The combined organic phase was washed with brine, dried over sodium sulfate and purified by column chromatography to afford 6.1 g of 4-(3-{5-chloro-1-(diphenylmethyl)-2-[2-({[2-(trifluoromethyl)benzyl]sulfonyl}amino)ethyl]-1H-indol-3-yl}propyl)benzoic acid methyl ester as a white foam (47% yield). $^1$H NMR (400 MHz, CDCl$_3$), δ 1.88-2.00 (m, 2 H), 2.64-2.77 (m, 6 H), 2.83-2.95 (m, 2 H), 3.90 (s, 3 H), 4.05 (t, J=5.9 Hz, 1 H), 4.33 (s, 2 H), 6.49 (d, J=8.8 Hz, 1 H), 6.70-6.88 (m, 2 H), 7.04 (dd, J=6.4, 2.7 Hz, 4 H), 7.24 (s, 1 H), 7.28-7.35 (m, 7 H), 7.36-7.49 (m, 3 H), 7.55-7.71 (m, 2 H), 7.95 (d, J=8.1 Hz, 2 H).

Step 3: The resulting ester (2.6 g, 3.4 mmol) was hydrolyzed by stirring with 1N NaOH in THF and enough MeOH to produce a clear solution. The reaction was monitored by TLC for the disappearance of starting material. When the reaction was complete, the mixture was concentrated, diluted with H$_2$O, and acidified to pH 2-4 using 1 M HCl. The aqueous phase was extracted with EtOAc and the organic phase was washed with brine, dried over sodium sulfate, and concentrated to afford 2.25 g (88%) of the title product, a yellow solid. $^1$H NMR (400 MHz, DMSO-d$_6$), δ 1.81-1.97 (m, 2 H), 2.66-2.79 (m, 4 H), 2.95 (s, 4 H), 4.41 (s, 2 H), 6.45 (d, J=8.8 Hz, 1 H), 6.78 (dd, J=8.8, 2.0 Hz, 1 H), 7.01-7.14 (m, 5 H), 7.24-7.42 (m, 8 H), 7.46 (d, J=2.0 Hz, 1 H), 7.50-7.66 (m, 4 H), 7.73 (d, J=7.8 Hz, 1 H), 7.85 (d, J=8.3 Hz, 2 H), 12.77 (s, 1 H); HRMS: calcd for C$_{41}$H$_{36}$ClF$_3$N$_2$O$_4$S+H+, 745.21092; found (ESI-FTMS, [M+H]$^{1+}$), 745.2132; Anal. Calcd for C$_{41}$H$_{36}$ClF$_3$N$_2$O$_4$S: C, 66.08; H, 4.87; N 3.76. Found: C, 66.07; H, 4.57; N, 3.67.

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention.

It is intended that each of the patents, applications, and printed publications, including books, mentioned in this patent document be hereby incorporated by reference in their entirety.

What is claimed is:

1. A synthetic process comprising reacting a compound of Formula II:

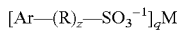
[Ar—(R)$_z$—SO$_3^{-1}$]$_q$M    II wherein:
Ar is phenyl substituted with one perhaloalkyl group at the 2 position thereof;
R is methylene;
each R$^1$ and R$^2$ is independently selected from the group consisting of H, C$_1$-C$_6$ alkyl and C$_3$-C$_7$ cycloalkyl;
or any R$^1$ and R$^2$, together with the nitrogen atom to which they are attached, can form a 5- or 6-membered heterocycle;
each R$^3$ is independently selected from the group consisting of H, C$_1$-C$_6$ alkyl and C$_3$-C$_7$ cycloalkyl;
M is a Group I or II metal ion;
q is 1 where M is Group I metal ion;
or q is 2 where M is a Group II metal ion; and
z is 1;
with oxalyl chloride in the presence of a catalytic amount of water and in the presence of a co-catalyst for a time and under conditions sufficient to form a compound of Formula III:

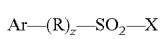
Ar—(R)$_z$—SO$_2$—X    III wherein X is Cl and Ar, R and z are as defined above.

2. The process of claim 1 wherein said reacting of said compound of Formula II with said oxalyl chloride is carried out in a solvent system comprising a solvent selected from the group consisting of an aprotic organic solvent; a polar aprotic organic solvent; a nonpolar aprotic organic solvent; a water-miscible aprotic organic solvent; and a water-immiscible aprotic organic solvent.

3. The process of claim 2 wherein said solvent system comprises one or more of tetrahydrofuran, acetonitrile, N,N-dimethylformamide, dioxane, acetone, toluene, methylene chloride, 1,2-di-chloroethane, methyl t-butyl ether, or ethyl ether.

4. The process of claim 2 wherein said solvent system comprises tetrahydrofuran.

5. The process of claim 1 wherein said co-catalyst is N,N-dimethylformamide.

6. The process of claim 1 wherein said reacting of said compound of Formula II with said oxalyl chloride is carried out at a temperature of less than about 5° C.

7. The process of claim 1 wherein the molar ratio of said catalytic amount of water to said compound of Formula II is less than about 0.5:1.

8. The process of claim 1 wherein the molar ratio of said catalytic amount of water to said compound of Formula II is of a value of from about 0.2 to about 0.4.

9. The process of claim 1 wherein the molar ratio of said catalytic amount of water to said compound of Formula II is about 0.3.

10. The process of claim 1 wherein the molar ratio of said oxalyl chloride to said compound of Formula II is about 1.2 or greater.

11. The process of claim 1 wherein Ar is 2-trifluoromethylphenyl.

12. The process of claim 1 wherein M is Na$^+$ ion or K$^+$ ion.

13. The process of claim 1 wherein M is Na$^+$ ion.

14. The process of claim 1 wherein:
Ar is phenyl substituted with one perhaloalkyl group at the 2 position thereof;
R is methylene;
M is Na$^+$ ion or K$^+$ ion;
X is Cl;
q is 1; and
z is 1.

15. The process of claim 1 wherein:
said co-catalyst is N,N-dimethylformamide; and
the molar ratio of said catalytic amount of water to said compound of Formula II is of a value of between about 0.2 to about 0.4.

16. The process of claim 1 wherein:
Ar is phenyl substituted with one perhaloalkyl group at the 2 position thereof;
R is methylene;
M is Na$^+$ ion or K$^+$ ion;
X is Cl;
q is 1;
z is 1;
said co-catalyst is N,N-dimethylformamide;
the molar ratio of said oxalyl chloride to said compound of Formula II is from about 2 to about 3; and
the molar ratio of said catalytic amount of water to said compound of Formula II is between about 0.2 to about 0.4.

17. The process of claim 16 wherein Ar is 2-trifluoromethylphenyl.

18. The process of claim 1 further comprising reacting said compound of Formula III with an amine reagent optionally in the presence of a base for a time and under conditions sufficient to form a compound of Formula I:

$$Ar-(R)_z-SO_2-NR^4R^5 \qquad I$$

wherein:

R$^4$ and R$^5$ are each, independently, H, C$_1$-C$_{18}$ alkyl, C$_2$-C$_{18}$ alkenyl, C$_2$-C$_{18}$ alkynyl, C$_3$-C$_{18}$ cycloalkyl, heterocycloalkyl, aryl or heteroaryl, wherein each of R$^4$ and R$^5$ is, independently, unsubstituted or substituted by up to five substituents independently selected from the group consisting of halogen, C$_1$-C$_6$ alkyl, C$_3$-C$_7$ cycloalkyl, heterocycloalkyl, cyano, nitro, OH, C$_1$-C$_6$ alkoxy, C$_1$-C$_6$ haloalkyl, C$_1$-C$_6$ haloalkoxy, aryl and heteroaryl;

or R$^4$ and R$^5$, together with the nitrogen atom to which they are attached, can form a 5- or 6-membered heterocycle and Ar, R and z are as defined above.

19. The process of claim 18 further comprising removing or destroying excess halogen substitution reagent prior to reacting of said compound of Formula III with said amine reagent.

20. The process of claim 19 wherein said destroying of said excess halogen substitution reagent is facilitated by adding water.

21. The process of claim 18 wherein said reacting of said compound of Formula III with said amine reagent is carried out at a temperature of less than about −10°C.

22. The process of claim 18 wherein said amine reagent is NH$_3$ or NH$_4$OH.

23. The process of claim 22, wherein said amine reagent is gaseous ammonia, and said reacting of said compound of Formula III with said amine reagent is carried out in a solvent system comprising an organic solvent and a small amount of water.

24. The process of claim 18 wherein the amine reagent has the Formula HNR$^4$R$^5$.

25. The process of claim 18 further comprising isolating said compound of Formula I.

26. The process of claim 18, wherein said compound of Formula I is formed without isolation of said compound of Formula III.

* * * * *